United States Patent [19]

Lassen

[11] 4,256,111
[45] Mar. 17, 1981

[54] FILAMENTS OF CHEMICALLY MODIFIED CELLULOSE FIBERS AND WEBS AND PRODUCTS FORMED THEREFROM

[75] Inventor: Frederick O. Lassen, Neenah, Wis.

[73] Assignee: Kimberly-Clark Corporation, Neenah, Wis.

[21] Appl. No.: 402,311

[22] Filed: Oct. 1, 1973

[51] Int. Cl.³ .................... A61F 13/20; B32B 5/02
[52] U.S. Cl. .................................... 128/284; 8/116 P; 8/120; 8/181; 128/285; 260/17.4 GC; 260/17.4 CL; 428/224; 428/364; 428/365; 536/34; 536/62; 536/84
[58] Field of Search ............... 161/157, 172, 265, 267; 260/17.4 GC, 17.4 CL, 231 CM, 212, 219; 428/364, 224, 370, 365; 264/176 F, 207, 108, 184; 8/116 P, 130.1, 120, 181; 128/287, 290 R, 284, 296, 285, 185; 536/34, 62, 84

[56] References Cited

U.S. PATENT DOCUMENTS

| 2,087,981 | 7/1937 | Lilienfield | 18/54 |
|---|---|---|---|
| 2,687,944 | 8/1954 | Johnson et al. | 264/187 |
| 2,829,944 | 4/1958 | Houtz et al. | 264/207 |
| 3,046,078 | 7/1962 | Salsbury et al. | 260/17.4 GC |
| 3,105,491 | 10/1963 | Harwood | 128/290 |
| 3,194,727 | 7/1965 | Adams et al. | 260/17.4 GC |
| 3,366,582 | 1/1968 | Adams et al. | 260/17.4 GC |
| 3,402,231 | 9/1968 | Bynum et al. | 264/184 |
| 3,423,925 | 1/1969 | George et al. | 57/164 |
| 3,565,886 | 2/1971 | Clermont | 260/219 |
| 3,589,364 | 6/1971 | Dean et al. | 162/146 |
| 3,617,437 | 11/1971 | Bagg et al. | 264/108 |
| 3,639,331 | 2/1972 | Hahori et al. | 264/108 |
| 3,658,790 | 4/1972 | Bernardin | 260/219 |
| 3,669,916 | 6/1972 | Nakao et al. | 260/17.4 GC |
| 3,670,069 | 6/1972 | Mitchell et al. | 161/177 |
| 3,691,154 | 9/1972 | Bernardin | 260/219 |
| 3,847,636 | 11/1974 | Smith | 106/168 |
| 3,858,585 | 1/1975 | Chatterjee | 128/290 |

FOREIGN PATENT DOCUMENTS 673367 6/1952 United Kingdom.

Primary Examiner—Paul J. Thibodeau
Attorney, Agent, or Firm—William D. Herrick; Raymond J. Miller; Howard Olevsky

[57] ABSTRACT

Chemically modified cellulose fibers such as those which have been subjected to phosphorylation or carboxymethylation or to polymer grafting-hydrolysis are refined in the presence of water, centrifuged to remove unbound water and extruded into filaments. The individual fibers are identifiable within the filaments and are generally aligned parallel to the filament axis. Certain embodiments of the filaments are highly absorbent, have fast wicking rates, and may be self-bonded to form integral nonwoven webs for use in disposable diapers, sanitary products, wipers and the like.

15 Claims, 18 Drawing Figures

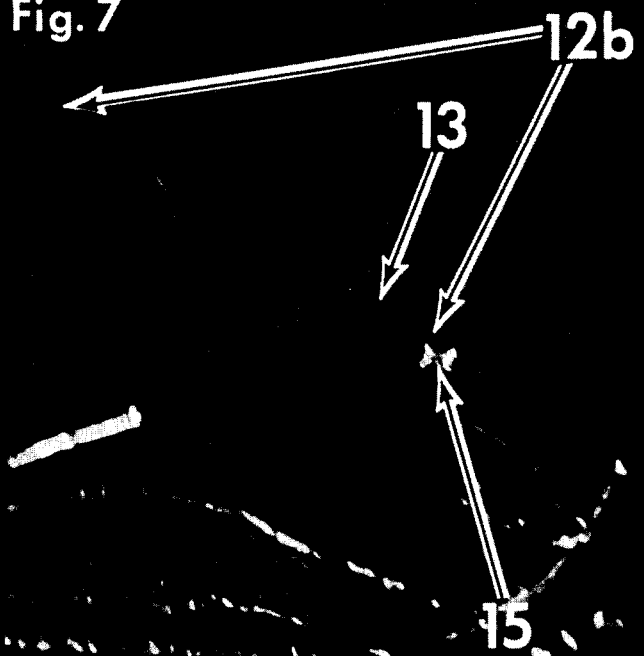
Fig. 7

FILAMENTS OF CHEMICALLY MODIFIED CELLULOSE FIBERS AND WEBS AND PRODUCTS FORMED THEREFROM

BACKGROUND OF THE INVENTION

1. Field of the Invention

This invention relates to highly absorbent filaments and webs as well as methods for making them. More specifically, it pertains to filaments of chemically modified cellulose fibers and webs constructed from such filaments that exhibit, for aqueous systems, high absorbency and wicking properties which can be controlled and varied from slow to very fast making them particularly suitable for applications where it is desirable to draw a liquid away from a surface and concentrate it in a particular layer or location. Such applications include, by way of example and not limitation, disposable diapers, sanitary napkins, wipes, surgical sponges and the like.

2. Description of the Prior Art

The chemical modification of cellulose to increase its absorbency has been previously described and can be considered in a broad sense to fall into three major classifications in terms of methods:

(a) chemical substitution, etherization or esterification;

(b) chemical substitution plus crosslinking; and (c) polymeric grafting.

For example, U.S. Pat. No. 3,670,069 to Mitchell is directed to absorbent fibers formed by extruding solutions such as those prepared from a hydroxyalkyl cellulose. As examples of category "(a)" above, Bernardin U.S. Pat. Nos. 3,658,790 and 3,691,154 disclose absorbent fibers and batt-like mats formed from phosphorylated cellulose or its acid form and products incorporating them. An example of category "(b)" above is U.S. Pat. No. 3,589,364 to Dean et al which discloses absorbent structures including cross-linked fibers of carboxymethyl cellulose and products made therefrom. Category "(c)" above is exemplified by the formation of acrylonitrile-grafted cellulose absorbent fibers and products as disclosed in U.S. Pat. Nos. 3,194,727 to Adams et al; 3,455,643 to Gruber et al; 3,065,041 to Suen; and 3,046,078 to Salsbury.

SUMMARY OF THE INVENTION

The present invention provides filaments of chemically modified cellulose fibers and webs of such filaments that not only are highly absorbent but can also be designed to exhibit a remarkable degree of wicking power, that is, the ability to rapidly draw aqueous liquids and concentrate them in a specific layer or location. The fibers are preferably formed into filaments by extruding them while in a highly swollen form followed by solvent drying. In the filaments, the individual fibers are predominantly generally aligned along a direction parallel to the filament length and form channels or capillaries for transporting the aqueous liquid. By randomly depositing the filaments onto a moving surface prior to drying, contact bonds or fused bonds between them can be formed, depending upon the desired end product properties, at crossover points resulting in a nonwoven web. These filaments and webs may be used as components or layers in such products as hospital or other medical products, disposable diapers, wipes, or sanitary napkins. Batts made from chopped filaments, when locally wetted, tend to form localized fluid resisting dams which can be used to prevent excess fluid from unwanted distribution. The process of the invention allows rapid and continuous solvent drying with improved economics, particularly when a solvent recovery system is utilized.

The form and quantity of the filaments of the invention used in specific embodiments may vary widely depending upon factors such as bonding, total composition, absorbency requirements and strength or other physical properties. When desired the webs may be reinforced as by means of a scrim or the like. The filaments or other structural components of the invention may be arranged in many combinations. For example, they may be blended into a homogenous mass or formed into laminar structures. Bonding methods such as contacting the filaments while still plasticized or tacky, needle punching, and adhesive coating (pattern or saturation) can be used. Also, a somewhat more flexible web can be produced by point bonding the web after it has been dried. A patterned nip can be used to form the point bonds. Pressing the dried web will improve its smoothness and ability to be wound upon itself and unwound.

The absorbency and wicking properties of the filaments and webs of the invention may be controlled within wide limits by varying parameters such as fiber refining, pH of swollen fiber compositions, and starting materials. In addition, the filaments are stronger and less subject to linting then are known forms of such highly absorbent fibers as well as having controlled interfiber adhesion and placement of absorbent material lacking in such other forms.

BRIEF DESCRIPTION OF THE DRAWINGS

FIGS. 6 and 7 are views similar to FIGS. 4 and 5 taken of swollen phosphorylated cellulose fibers;

DESCRIPTION OF THE PREFERRED EMBODIMENTS

In order to ensure a complete understanding of the present invention the intended meaning of certain terms used in the description will now be stated;

"Chemically modified cellulose" refers to cellulosic materials the composition and/or structures of which have been transformed by derivatization in such a way as to induce a significant increase in their hydrophilic character. Examples of derivatization processes include carboxylation, phosphorylation, and grafting of acrylic segments. The present invention is not concerned with cellulosic solutions or other cellulosic compositions in which the individual fibers or other basic structures themselves, lose their identity;

"Highly absorbent" as used herein indicates that the modified cellulose will absorb significantly more of the liquid being used than will unmodified cellulose under the same conditions. It is recognized that the particular absorbency rating will depend not only on the specific material tested but on the conditions under which the measurements are made. For example, the absorbency of a material under pressure may be quite different from its absorbency in an uncompressed state.

"Fibers" is used herein in reference to the fibers of chemically modified cellulose that make up the filaments of the invention; for cost considerations they have a length preferably of about papermaking fiber size, e.g., about 0.146 inch and a diameter preferably about 0.002 to 0.003 inch although longer fibers such as cotton linters may be used.

"Filaments" as used herein means elongated strands composed of interbonded, generally aligned fibers;

"Water retention" is defined in U.S. Pat. No. 3,670,069 to Mitchell et al, at col. 6, lines 51 to 70, as the moisture remaining in and on a rewet fiber specimen after it has been centrifuged for 10 minutes at an acceleration of 1000 times normal gravitational acceleration;

"Extrudate" refers to a mass of extrudable, hydrophilic, fibrous cellulosic material which has been swollen by the imbibition of a solvent to such an extent as to plasticize the individual cellulosic fibers and render them independently mobile;

"Contact bond" is defined as a surface bond formed between filaments at locations where they touch. The integrity and alignment of each filament is substantially maintained in the bond areas. Upon the application of tensile forces to the web, breaking preferentially occurs in the bond areas.

"Fused bond" is defined as a bond formed between filaments wherein they become welded or merged together in the bond area. The bond mass is integral and will not break any more readily than the filaments, themselves; and "Consistency" as used herein means weight percent swelling medium in any of the compositions or mixtures recited. All percentages are by weight unless otherwise noted.

Figure 1:
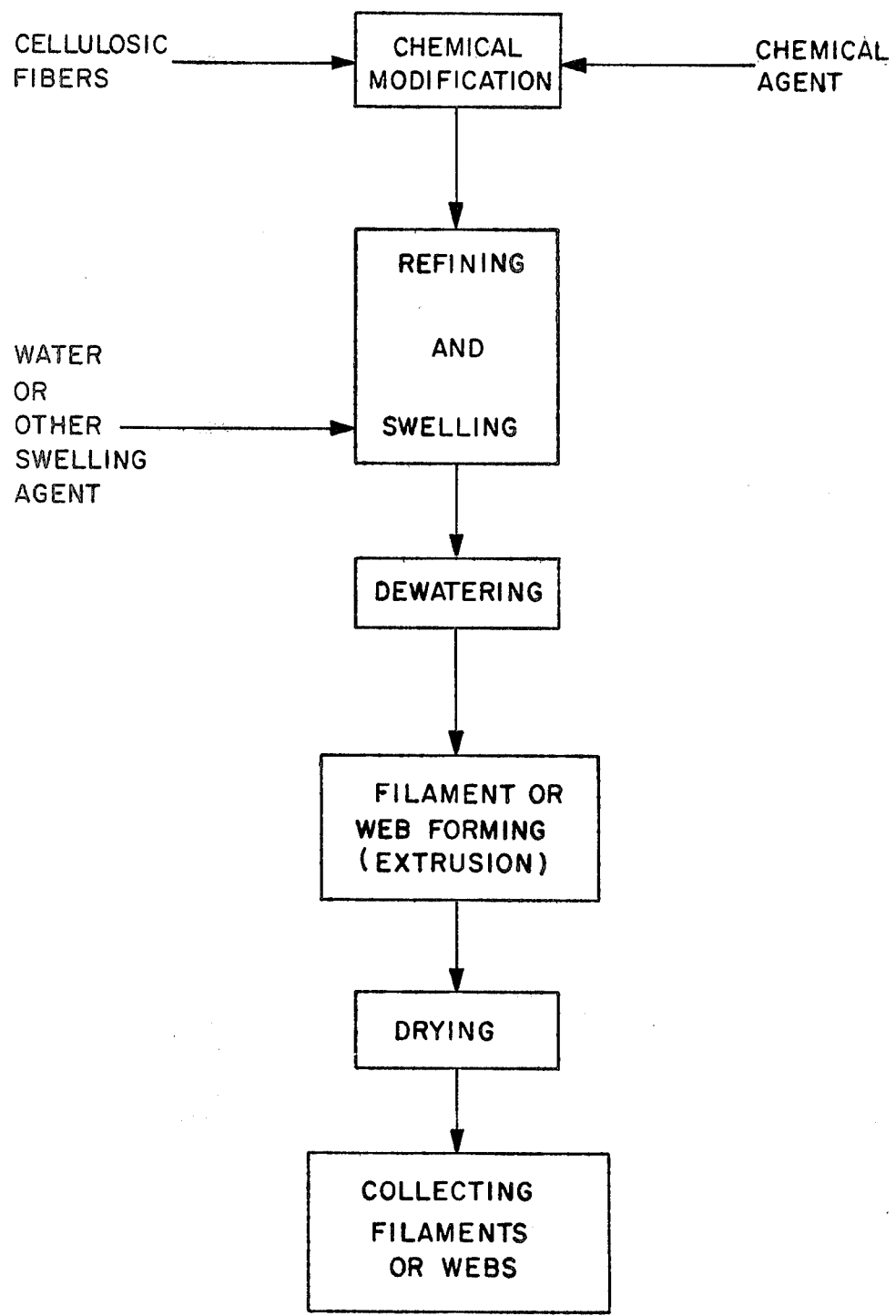
FIG. 1 is a flow diagram illustrating the preferred process for making the filaments and webs of the present invention.

In the process of the present invention as illustrated in FIG. 1, the first step is to provide chemically modified cellulose fibers. While commercially available products such as "Buckeye" carboxylated cellulose from Buckeye Corporation, for example, with modification may be useful in this process, the diversity of results which may be obtained is increased by beginning with pulp or wood fibers and treating them by phosphorylation, carboxylation, or acrylonitrile substitution as set forth in greater detail below.

One of the preferred types of chemically modified fibers for use in the present invention is phosphorylated pulp fibers. To produce such fibers the following process may be used although it will be recognized by those skilled in this art that variations and modifications of this process may also be utilized.

The particular pulp selected to be phosphorylated is not critical; for example, Northern spruce pulp is readily available, generally low in cost, and produces very acceptable results. The pulp may be used in dry sheet form as supplied by pulp manufacturers. The sheets are preferably immersed for about 15 to 45 minutes in a reagent composition containing about 50% urea and about 32% phosphoric acid, for example. The purpose of this immersion is to distribute these reagents evenly throughout the pulp, and it will be apparent that the time and reagent concentration may be varied within wide ranges depending upon factors such as speed of operation and desired degree of phosphorylation. For example, to obtain a 6% or better phosphorylation, a pickup of approximately 200% to 300% of the above reagent solution should be achieved. It is preferred to maintain the treating bath at a somewhat elevated temperature, for example, 60° C. to 70° C. to facilitate the penetration of the pulp boards.

After immersion the pulp is cured at a temperature within the range of from about 125° C. to about 195° C. and preferably 180° C. to 190° C. Since the purpose of heating is to make energy available for the phosphorylation reaction, the amount of time required for this step depends upon the form and intensity of the applied energy as well as the quantity of pulp and the concentration of reagent therein. For example, the curing of wood pulp in an oven at 185° C. is preferably terminated when the pulp has turned light brown in color. On the other hand, the curing may be greatly accelerated by the use of a microwave oven in which case the temperature of the pulp provides an indication of its cure state, and the curing is terminated when the temperature of the pulp rises after having first maintained a generally constant level. The use of microwaves also generally results in somewhat softer filaments and webs with very little of the discoloration which results from standard oven curing and is preferred for these reasons as well as reduced cure time.

After curing, the phosphorylated pulp is washed to remove excess reagents. It is then hydrolyzed with a dilute acid, preferably hydrochloric acid (2% to 5% by weight, for example). In some cases, depending upon the pulp used, hard fiber clumps may be present, and mild agitation may be used to break or soften them. Hydrolysis at a temperature of about 50° C. to 90° C. and preferably 60° C. to 70° C. for onehalf hour to two hours is usually sufficient, after which the phosphorylated pulp is washed again with water.

The resulting hydrolyzed phosphorylated pulp is in its acid form and next is converted to its salt form by contact with an excess of base, for example, sodium carbonate (3 to 6% by weight). Preferably this contact takes place under conditions of agitation for at least about 15 minutes at room temperature. After washing to remove excess base, the phosphorylated pulp is in its preferred chemically modified form.

With phosphorylated pulp or other types of chemically modified cellulose, when it is desired to produce a filament with high wicking rates, containment capacity, or the ability to absorb and retain large quantities of liquid, the next step is preferably refining of the chemically modified pulp. While it is not desired that the invention be limited to any particular theory, it is believed that the refining breaks away the outer shell, or primary wall of the fiber thus allowing it to expand and absorb more liquid as shown in FIGS. 4 through 7, for example. In any event, the degree of refining is an important factor in tailoring the final filament properties. By varying such conditions as pulp quantity, water content, frictional pressure in the refiner, and refining time, the desired fiber refinement may be obtained. In general, the higher the fiber quantity (lower the water content) the less the fibers will be refined for a given time and blade pressure. On the other hand, increasing either or both the refining time or frictional pressure will result in a greater degree of fiber refinement.

When refining has been completed, the individual fibers, while retaining their identities, are in a highly swollen, gel-like form. At this point, particularly where physiological effects are to be considered, the pH of the fibers is adjusted to within the range of from about 4 to 9 and preferably 5.5 to 8 by the addition of dilute acid or base as needed. It will be recognized that this step may be carried out at a different time in the overall process or omitted entirely where medical clearance is not needed.

The filament forming or spinning step offers a second opportunity to tailor final filament properties. In accordance with the invention it has been found that the individual fibers will retain their identities when the refined swollen material is extruded and generally become aligned to form an integral filament. The orifice through which the extrudate is extruded will have a significant effect on the filament properties. The lower limit for orifice cross-section is believed to be about that of the individual fiber, itself, recognizing that filament integrity will decrease when the filament diameter is so reduced. Filaments have been formed from orifices as low as 0.005 inch in diameter. In general, for batches of equally refined swollen fibers and up to a diameter of 0.035 inch, the larger the orifice, the better will be the wicking properties of the resulting filament in terms of its ability to transport a liquid from one location to another along its length. This is believed to be due to the larger number of channels which remain within the filament when its component swollen fibers are collapsed although, again, it is not desired to limit the invention to any particular theory. The finer filaments tend to exhibit a faster rate of absorption which is believed to be due to their larger surface area per given weight of filaments. There is not believed to be any upper limit to the orifice size except that the degree of alignment of the fibers within the filaments will, of course, be less as the filaments get larger. Filaments with good wicking properties have been formed from orifices 0.060 inch diameter and larger. The particular shape of the orifice in crosssection is not believed to be critical, and the use of shapes other than circular is contemplated as a matter of choice.

The water content of the extrudate will, it has been found, affect the wicking properties of the extruded filament. For example, for 6% phosphorylated cellulose produced as above described, high wicking rates are obtained when the water content is preferably in the range of at least about 92% by weight at the time of extrusion while reduced water contents will generally result in more slowly wicking filaments. In terms of the physical filament properties, the optimum water consistency will vary somewhat with each production depending on the particular fibers, degree of refining, and processing history. For web forming, preferably the consistency is selected which will produce a filament that will support itself for a length of about three inches. Lower consistencies will generally result in longer, stringlike webs with loose contact bonds while higher consistencies produce short, weaker, fuse-bonded webs. Of course, the effect of water content will vary depending on the particular composition. As formed, the filaments contain about 85% to 99% water by weight and must be dried in order to provide sufficient strength and integrity for further handling.

Figure 2:
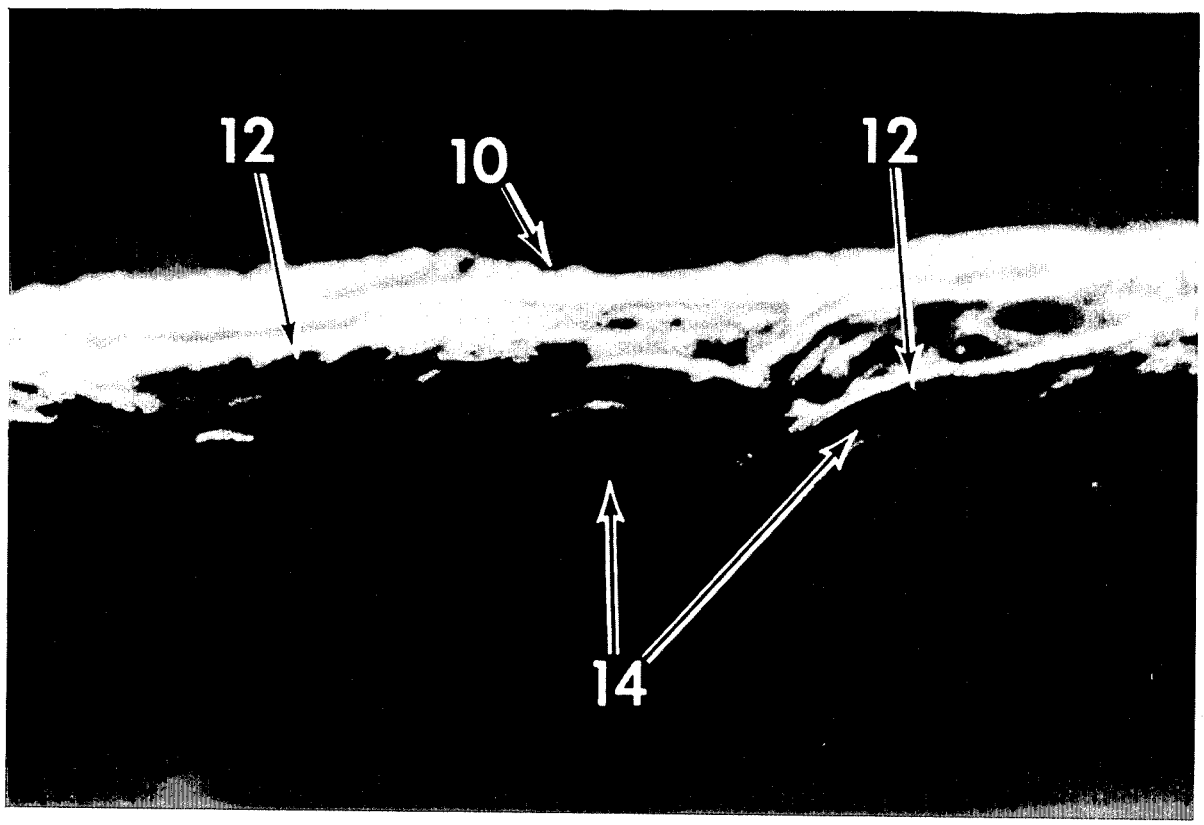
FIG. 2 is a photographic partial view of a filament of the invention prior to solvent exchange and drying and shown at a magnification of 92X.

Turning to FIG. 2, a filament formed in accordance with the invention will now be described in detail. As shown, the filament is in the form in which it appears immediately following extrusion and prior to drying. The photograph was taken at a magnification of 92X to illustrate more clearly the filament construction.

Filament 10 is composed of fibers 12 which are predominantly aligned generally parallel to the axis of the filament. The fibers are swollen and bonded within the filament by the cohesive nature of their gel-like outer surfaces depending upon the degree of refining.

The drying procedure, which involves both solvent exchange and evaporation, presents an additional opportunity to modify the final filament properties to produce a desired result. In accordance with the present invention, the filaments are preferably extruded directly into a solvent exchange bath. The selection of a solvent will substantially affect the softness and wicking properties of the resulting filaments. For example, filaments formed from swollen phosphorylated pulp fibers and dried in acetone are relatively soft, have fast wicking rates, and are very absorbent. The same filaments dried in methyl ethyl ketone, while harsher, exhibit similar absorbent capacities and may have more variable wicking rates. For a fast wicking product it is preferred that the filament be extruded directly into the solvent with a minimum of air contact since air drying prior to solvent exchange tends to produce a harsh, slowly wicking product. The time during which the filament is submerged in the solvent will depend upon the quantity of water to be removed, filament size and desired properties; however, it is preferred that the dried fibers contain less than 10% water. Further in accordance with the present invention, it has been found that agitation greatly increases the drying rate. For example, the use of ultrasonic agitation will reduce the preferred drying times to about ¼ that which is otherwise necessary. Moreover, it has been found that heating the extrudate prior to spinning also results in increased drying rates, so where high speed drying is desired, it is preferred to maintain the material being extruded at a temperature of up to about 100° C. A single solvent bath such as acetone may be used. For best results when the solvent is acetone, the bath is preferably less than 10 percent water by weight. In accordance with the invention, however, it is preferred that multiple solvent baths be utilized. In such a case it has been found that only the last bath need be maintained at less than 10 percent water when acetone is used. Similar results may be obtained with other solvents. Thus, in a continuous process, baths may be rotated from last to first with only the last bath requiring new solvent. The design of a solvent system will, of course, involve other considerations such as cost, feasibility of recovery, air pollution, and so forth. Examples of additional solvents which may be used include methyl-ethyl ketone, a mixture of chloroform and methanol, n-propanol, isopropanol, benzene-isopropanol, and others will be apparent to those skilled in this art.

Figure 3:
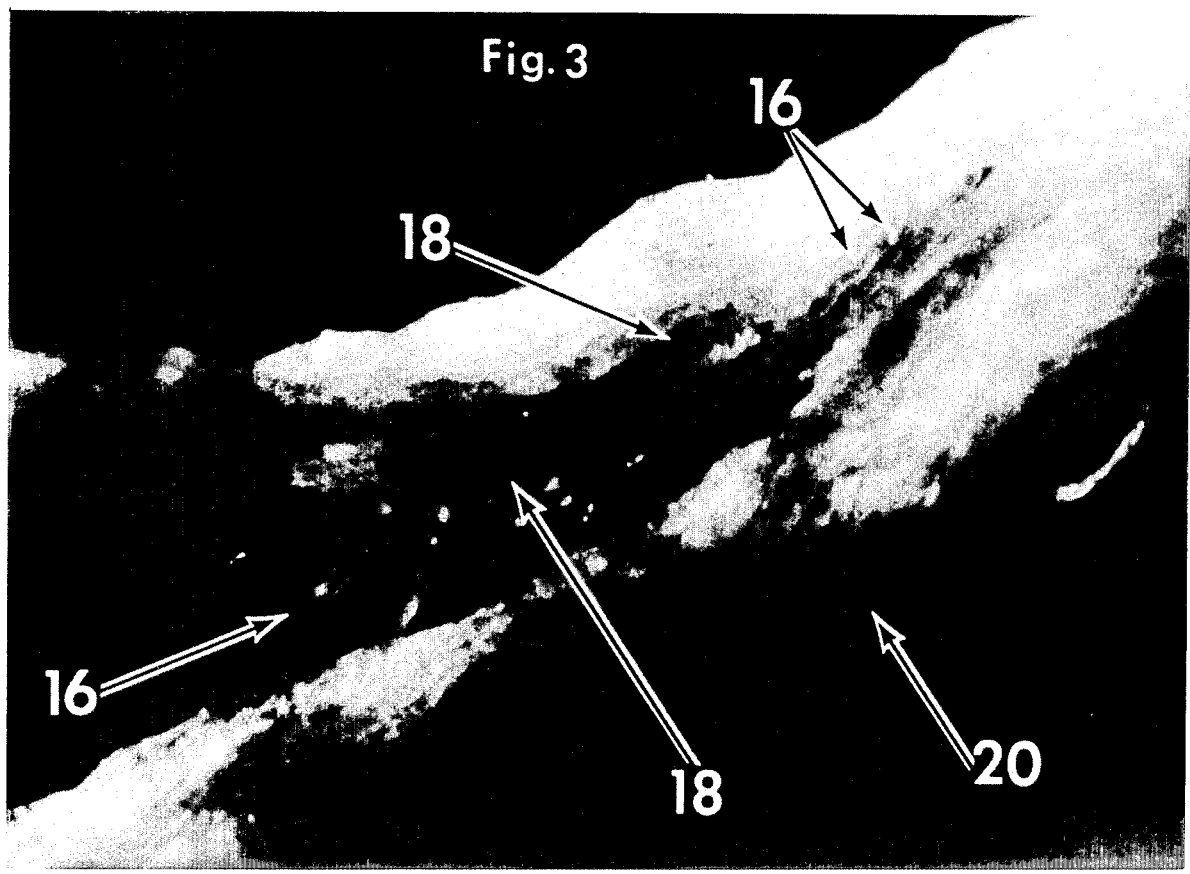
FIG. 3 is a view like that of FIG. 2 except that the filament has been solvent-dried.

FIG. 3 is a photograph showing at a magnification of 92X a phosphorylated cellulose filament as in FIG. 2 except that it has been solvent dried. As can be seen, the fibers 16 retain their generally aligned configuration although the swelling is greatly reduced. The reduction of the fiber diameter produced by the solvent exchange and drying results in interfiber bonding and interstices 18 between fibers 16 within dried filament 20.

Additional forms of chemically modified cellulose may be utilized. It is important, however, that the form selected be highly absorbent and capable of being made into an extrudable swollen form without completely dissolving or otherwise significantly destroying the basic structure of the individual cellulose fibers. Where a single type of chemically modified cellulose is to be utilized, preferably it is not extensively cross-linked, e.g. cross-linked to such an extent as to destroy the fibril characteristics which provide interfiber bonding during the drying process. Some highly cross-linked fibers such as the previously mentioned "Buckeye" carboxylated cellulose may, however, be mixed with other cross-linked fibers as long as the mixture contains at least about 2% by weight of some less cross-linked fibers which do possess the necessary internal bonding properties. In other cases, the interfiber bonding properties of the highly cross-linked fibers can be improved by this invention by refining the fibers in their swollen state to produce a more fibrilated fiber condition. These refined fibers may be formed in accordance with the invention into filaments without mixing with other fibers. In many cases, additional refining also generally improves the absorbency characteristics of these fibers.

The degree to which the fibers are chemically modified involves primarily a matter of choice depending upon the desired filament characteristics and type of chemical modification involved. In general, however, in the case of phosphorylated pulp, for example, at least about 3% phosphorous substitution is necessary to produce fibers which can be sufficiently swelled and formed into desirable filaments.

Figure 4:
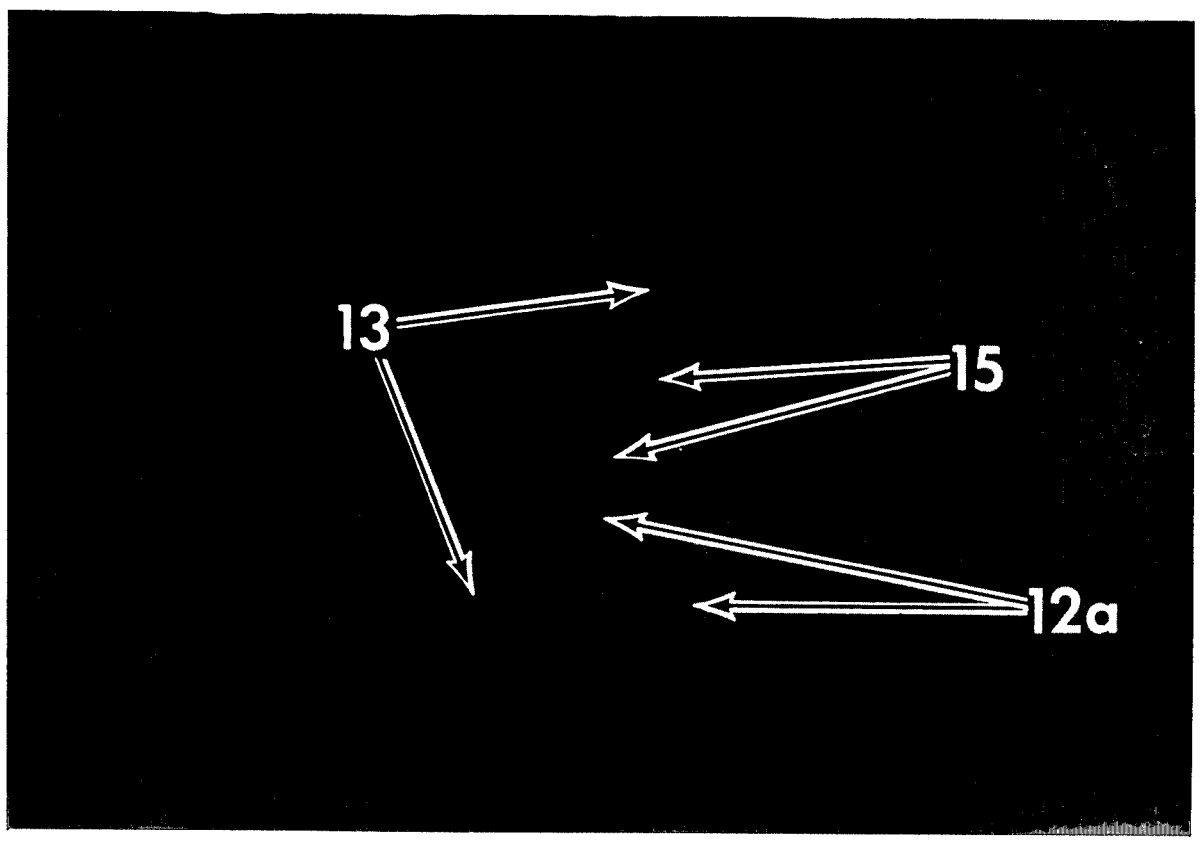
FIGS. 4 and 5 are enlarged photographic views of swollen acrylonitrile grafted cellulose fibers taken at magnifications of 108X and 392X respectively.
Figure 5:
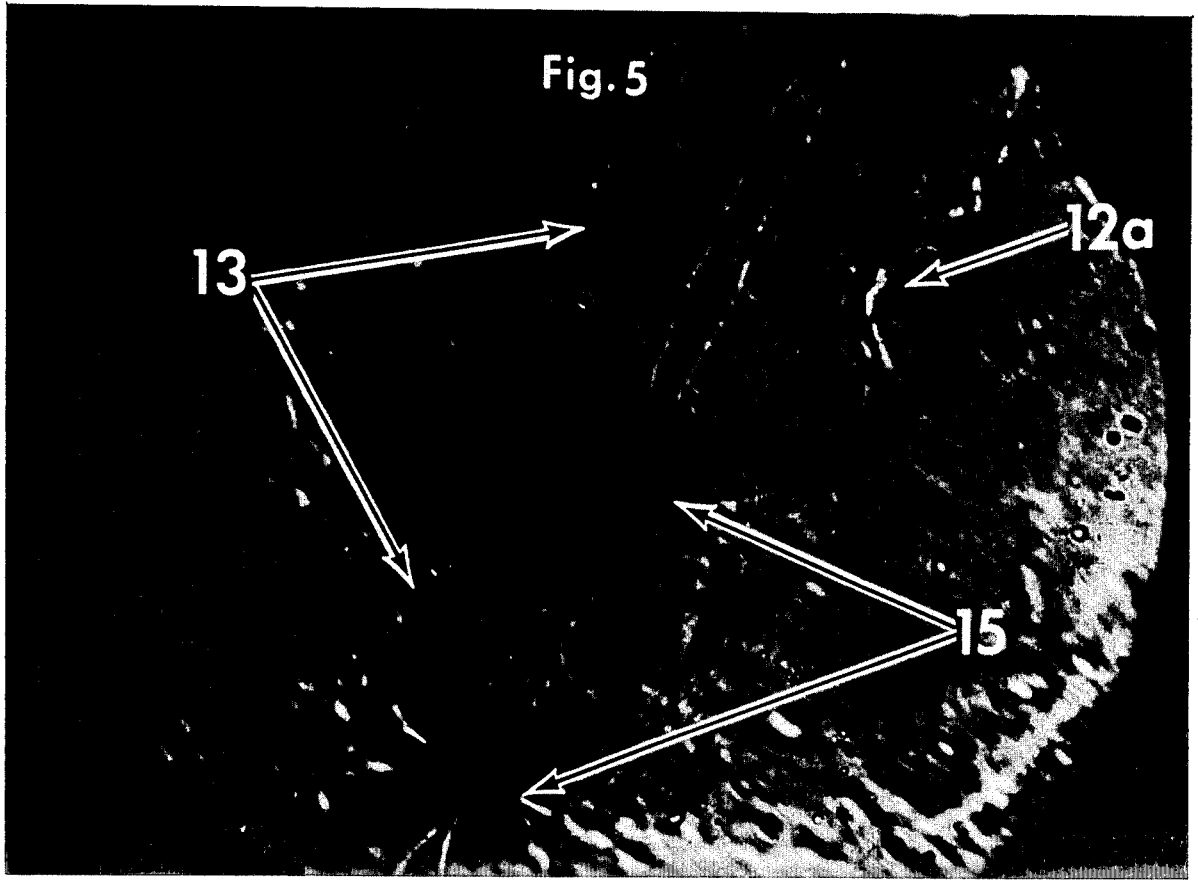

FIGS. 4 through 7, for example, illustrate fibers of the invention that are highly swollen, yet can be readily identified. The photographs of FIGS. 4 and 6 are taken at a magnification of 108X while the photographs of FIGS. 5 and 7 are taken at a magnification of 387X FIG. 5 is a view of the central portion of FIG. 4 showing acrylonitrile-grafted cellulose fiber 12A and illustrating the highly expanded portions 13 and rings 15 where refining has not completely broken away the fiber wall as above described. FIGS. 6 and 7 similarly depict a phosphorylated cellulose fiber 12B produced according to the above described process.

When a web is to be formed, the filaments may be combined prior to the drying step by directing them onto a moving screen which, in turn, carries the web into the solvent bath. Particularly when a solvent system such as acetone is utilized, this will result in the formation of interfilamentary bonds wherever filament crossings occur. The nature of these bonds is not clear and, while the invention is not to be limited to any particular theory, it is believed that the type of bonds formed depends upon the degree of plasticization or swelling of the individual fibers and/or the degree of surface drying occurring prior to filament contact. Fused bonds, therefore, will be formed between filaments composed of highly swollen and/or plasticized fibers while contact bonds will be formed between those which are composed of fibers that are lower in consistency or are in a less swollen or less plasticized form. In any event, the bonding is quite adequate to form a self-sustaining web with sufficient integrity to withstand further handling and processing without disintegration. The degree of bonding can have a significant effect on the wicking properties of the resulting web. In general, it has been found that a loosely bonded web will transport liquids faster than a highly bonded web, so where this property is important it is preferred to promote light, contact bonds.

Figure 8:
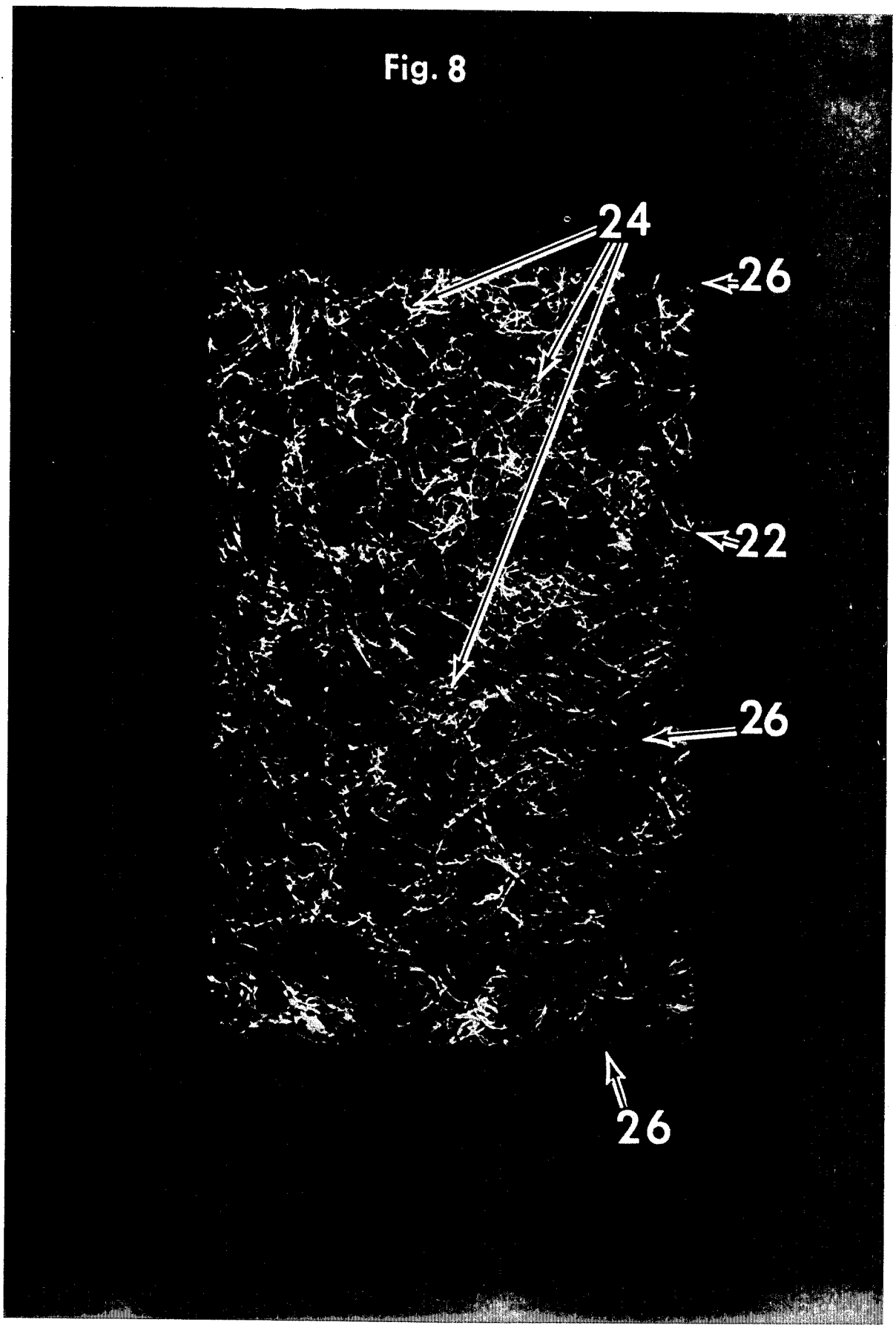
FIG. 8 is a photographic view of a contact bonded, nonwoven web formed from the filaments of the present invention shown at true size.
Figure 9:
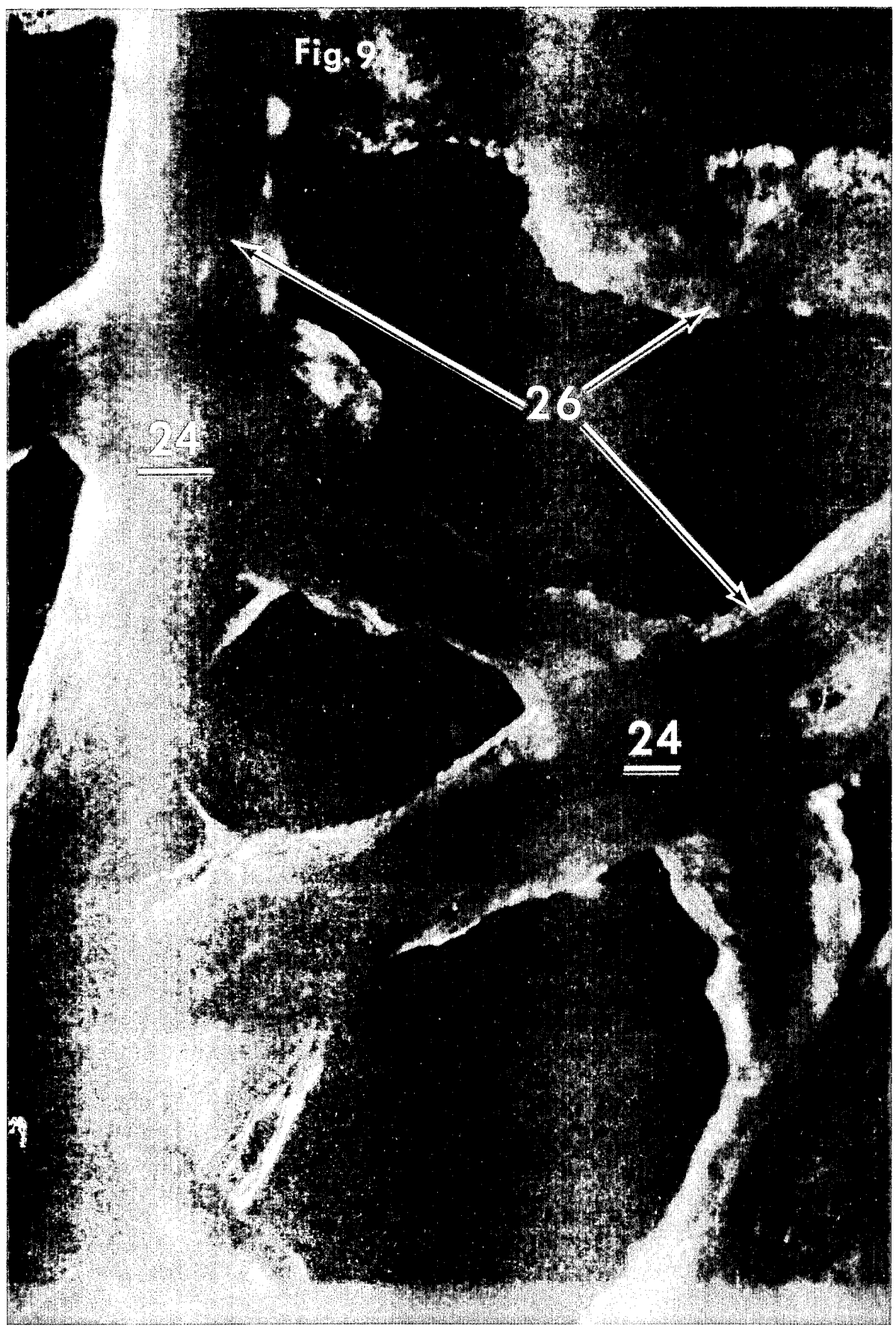
FIG. 9 is an enlarged photographic view of a contact bond as in the web of FIG. 6 at a magnification of 130X.

FIG. 8 is a photograph of a contact bonded web formed by randomly depositing phosphorylated filaments and solvent drying. The web 22 is on a black background for illustrative purposes so that contact bonds 24 between filaments 26 may be readily identified. FIG. 9 is a photograph of contact bonds 24 taken at a magnification of 130X showing that filaments 26 are distinguishable even in the bond areas.

Figure 10:
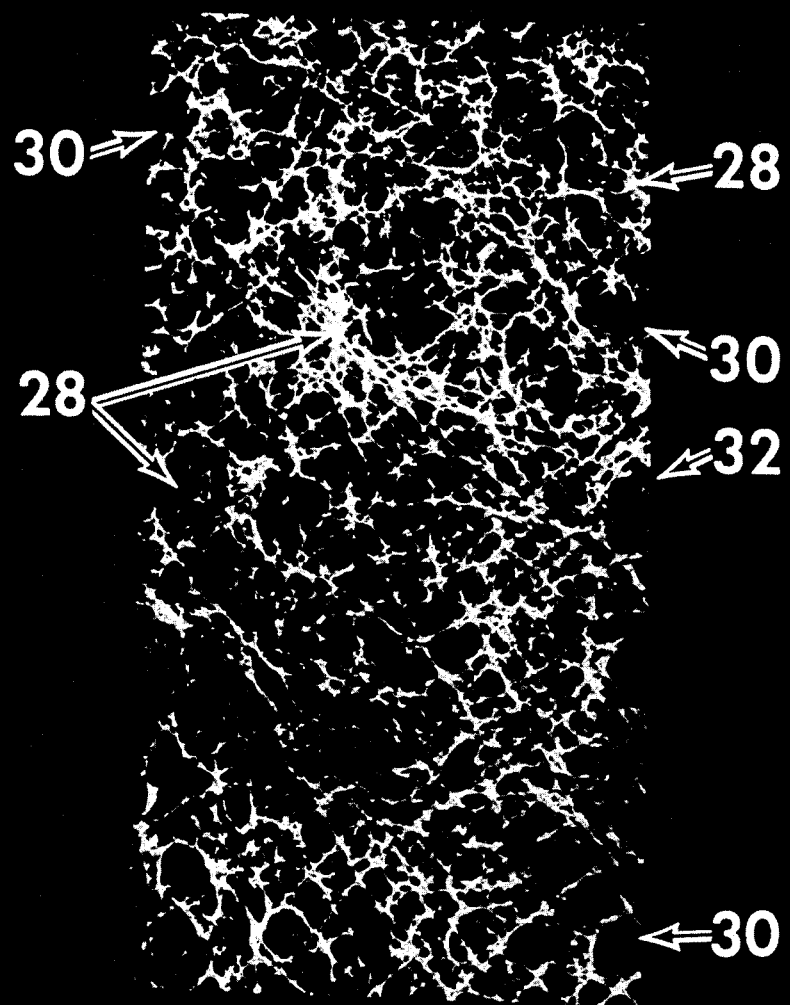
FIG. 10 is a view like that of FIG. 8 of a fused bonded web.

FIG. 10 is a photograph like that of FIG. 8 showing a fused bonded web. In this case fused bonds 28 tend to mask the individual filaments 30 in the web 32. This effect is shown more clearly in FIG. 11 which is a photograph showing fused bonds 28 at a magnification of 130X. The filaments tend to fuse or weld in the bond areas and produce a fibrous mass although the individual fibers still may be identified within the filaments 30.

EXAMPLE 1

A filament of phosphorylated cellulose was prepared in the following manner. Northern spruce pulpboards were soaked for ½ hour at 70° C. in a solution of 50% urea, 32% orthophosphoric acid, and 18% water by weight. They were then cured for 2 hours at 180° C.–190° C. in a forced-draft oven. Following a water wash, the fibers were treated for one hour with 3.7% HCl (w/w) at 60°–70° C. Following a water wash, the fibers were soaked in 5 to 10% $Na_2CO_3$(w/w) for ½ hour at room temperature. Then following a water wash, the fibers were refined in a standardized Valley beater, being hydro-refined for 30 minutes and mechanically refined for 3 minutes with 5 lbs. pressure on the beater blades. Following adjustment of the pH to 7.5 with dilute HCl, the unbound interfiber water was removed from the refined fibers by centrifugation at approximately 37,000 G using a Sharples Model M-41-24 ultracentrifuge. The dewatered fibers were then extruded into acetone through a 20 gauge (I.D. $\approx$ 0.022 inch) syringe needle to yield filaments. The filaments were removed from the acetone and any remaining acetone was evaporated off.

Reference may be made again to FIG. 2 for a photograph of such a filament prior to drying, and to FIG. 3 for a similar photograph taken subsequent to drying.

EXAMPLE 2

A web was formed by the extrusion of the swollen phosphorylated pulp extrudate described in Example 1, through a 20 gauge (I.D $\approx$ 0.022 inch) syringe needle onto a "Teflon" coated wire. This water swollen web was then collapsed by immersion into an acetone solvent exchange bath and dried by evaporating off the remaining acetone. The resulting solvent-dried web had an average weight of 0.022 gram/sq.in. and a moisture content of approximately 6 percent.

Reference may be made again to FIG. 8 for a photograph of a contact bonded web, and FIG. 9 for a contact bond in detail.

EXAMPLE 3

A filament of cross-linked carboxymethyl cellulose mixed with 10% phosphorylated pulp by weight was formed by mixing Buckeye brand cross-linked carboxymethyl cellulose (CMC) fibers into a slurry of refined phosphorylated pulp fibers (5.96% phosphorus w/w) in the ratio 9:1 by dry fiber weight, dewatering the resulting slurry by centrifugation at approximately 37,000 G in a Sharples Model M-41-24 ultracentrifuge, extrusion of the swollen fibers through a 20 gauge (I.D.≈0.022 inch) syringe needle to form a filament, subsequent solvent-drying of the filament with acetone, and evaporating off the remaining acetone from the filament.

EXAMPLE 4

A web was formed from filaments of carboxymethyl cellulose mixed with 10% phosphorylated pulp by weight by mixing Buckeye brand CMC fibers into a slurry of refined phosphorylated pulp fibers (5.96% phosphorus w/w) in the ratio 9:1 by dry fiber weight, dewatering the resulting slurry by centrifugation at approximately 37,000 G in a Sharples Model M-41-24 ultracentrifuge, extrusion of the resulting swollen fibers through an 18 gauge (I.D.≈0.031 inch) syringe needle to form a web, subsequent solvent-drying of the web with acetone, and evaporating off the remaining acetone from the web. The resulting web had an average weight of 0.012 gram/sq.in.

Figure 11:
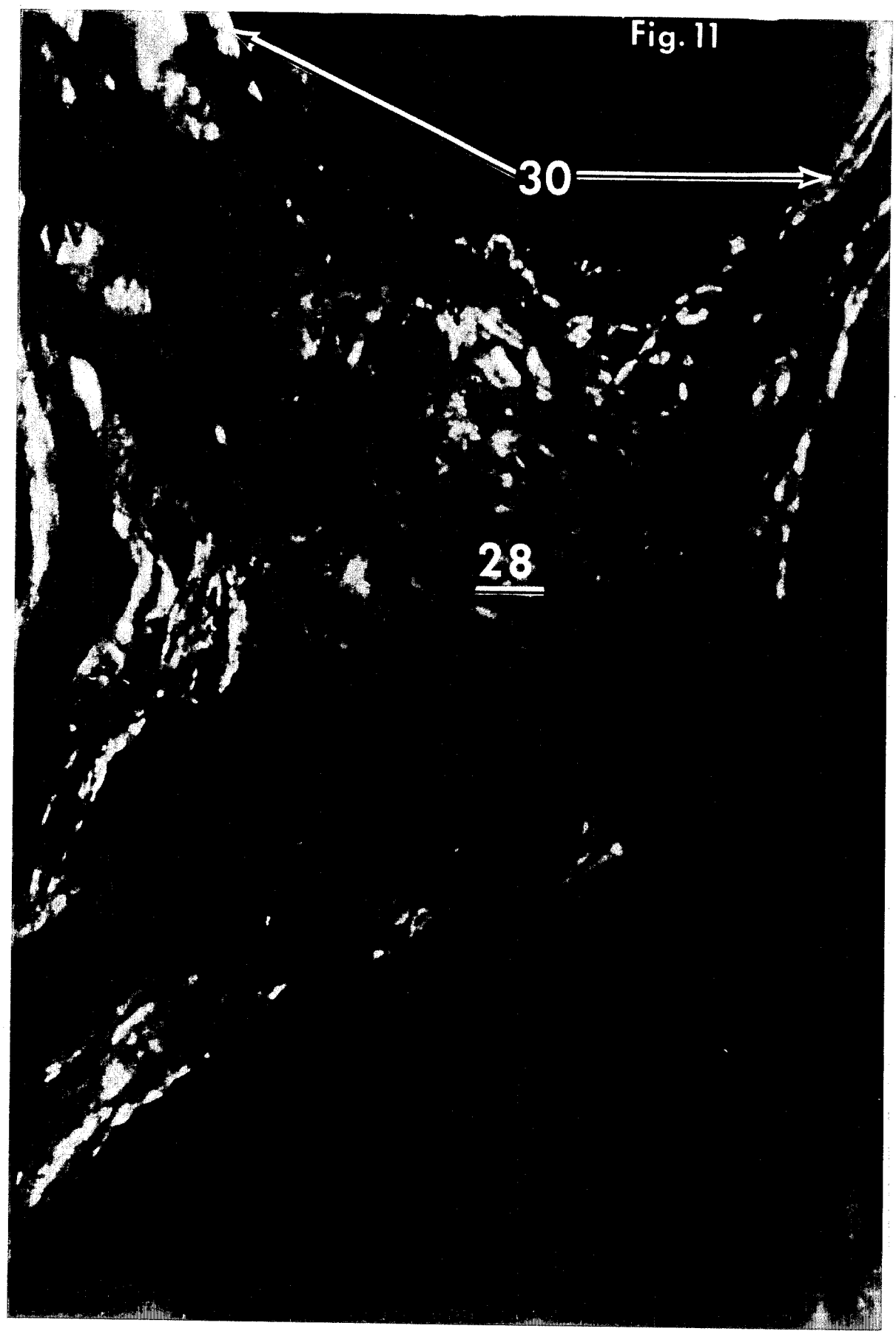
FIG. 11 is an enlarged view similar to FIG. 9 of a fused bond as in the web of FIG. 10.

Reference may be made again to FIG. 10 for a photograph of a fused bonded web while FIG. 11 is a detailed view of a fused bond.

EXAMPLE 5

Cotton linters (fibers of cotton generally having an average fiber length of 3.5-5.0 mm. and an average fiber diameter of 20 microns and constituting about 90% pure cellulose) were phosphorylated and extruded into filaments and a web in the following manner: cotton linters in the form of a pressed pad ⅛ inch thick were phosphorylated by the method of Example 1 to a yield of 5.4% phosohorus (w/w). Following the standard base conversion, the cotton linters were refined for 5 minutes in a PFI refiner, centrifuged at approximately 37,000 G in a Sharples Model M-41-24 ultracentrifuge to dewater after adjusting the pH to about 7.4, and extrusion of the swollen fibers through an 18 gauge (I.D.≈0.031 inch) syringe needle to form a web. Following solvent-drying with acetone, any remaining acetone was evaporated off. The resulting web had an average weight of 0.03 g./sq.in.

EXAMPLE 6

A web was formed from cross-linked carboxymethyl cellulose filaments by obtaining Buckeye fibers and making a slurry in water, circulating this slurry in a Valley beater for 8 minutes with no blade pressure, beating this slurry in a standardized Valley beater for 3 minutes with 5 lbs. suspended on the blades, centrifuging the resulting slurry of refined fibers at about 37,000 G to dewater, and extruding the swollen fibers through an 18 gauge (I.D.≈0.031 inch) syringe needle to form a web. Subsequently, the web was solvent dried in acetone, and the acetone remaining in the web was evaporated off. The resulting web had a weight average of 0.0111 g/sq.in.

EXAMPLE 7

A web was formed of hydrolyzed acrylonitrile grafted cellulose fibers by making a slurry of the grafted fibers (100% add on) and circulating them in a standardized Valley beater for 5 minutes with no blade pressure, centrifuging the resulting slurry of refined fibers at ≈37,000 G to dewater, and extruding the resulting highly plasticized, swollen fibers through a 20 gauge (0.022 inch) syringe needle to form a web. Subsequently the web was solvent-dried in acetone, and the remaining acetone evaporated off. The average weight of the resulting web was about 0.0032 g/sq.in.

EXAMPLE 8

In order to demonstrate the effect of varying the drying solvent composition, webs were formed in the manner of Example 2 but solvent dried in the following solvent compositions:
RUN A—100% acetone
RUN B—5% (w/w) n-propanol in acetone
RUN C—100% methyl ethyl ketone
RUN D—100% acetone followed immediately by 100% isopropanol
As Table I indicates, the hand and bonding characteristics of the resulting webs can be varied over wide ranges.

TABLE I

| Run | Bond | Hand |
| --- | --- | --- |
| A | Contact | good |
| B | small amount of contact bonding | very good - very soft |
| C | no bonding | very poor - very harsh |
| D | contact | very good - very soft |

EXAMPLE 9

In order to demonstrate the effect of varying the consistency of the swollen extrudate upon the absorbent filaments, webs were formed in the manner of Example 2 from phosphorylated pulp fibers with consistencies adjusted, prior to extrusion, to the following levels:
RUN A—96.66%; RUN B—94.11%; and RUN C—93.89%.

Figure 17:
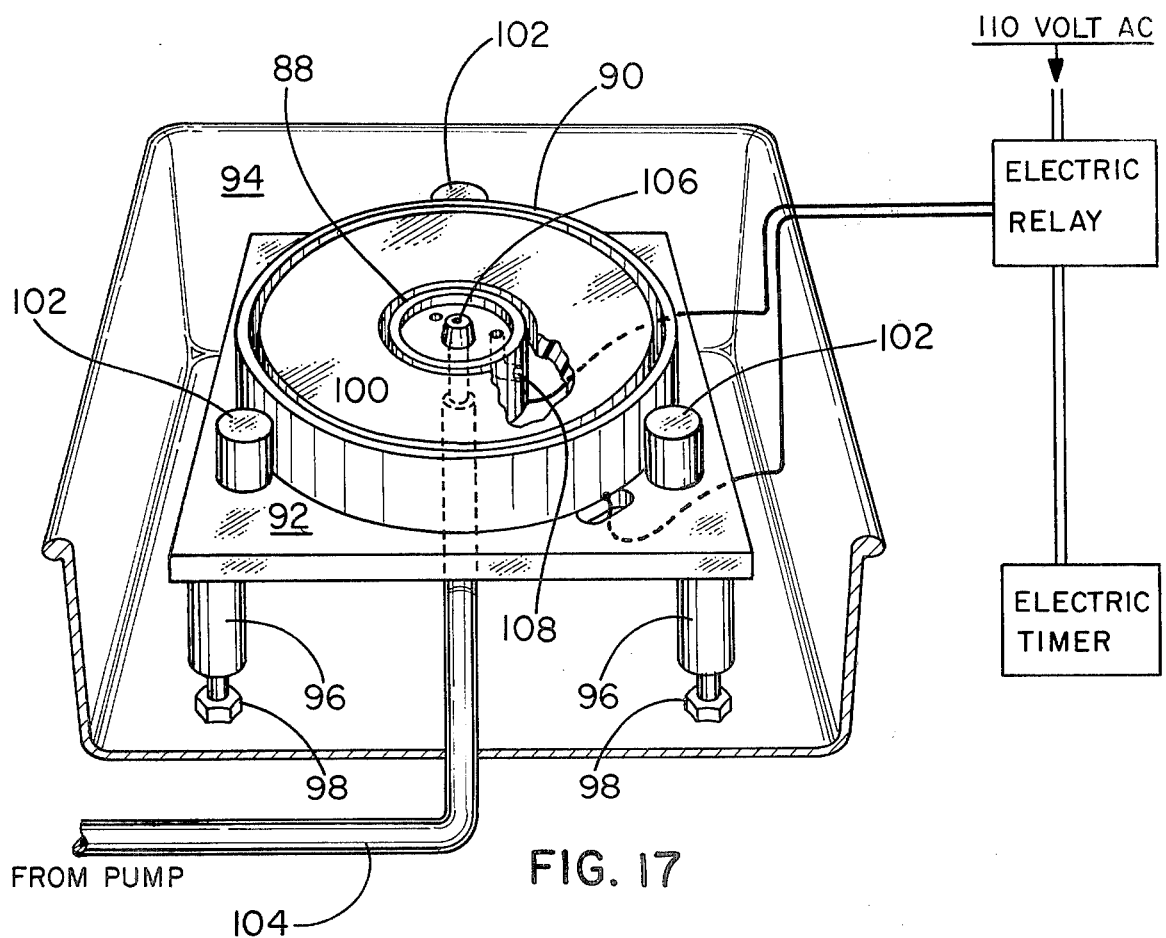
FIGS. 17 and 18 are schematic views of apparatus for obtaining wicking rates.
Figure 18:
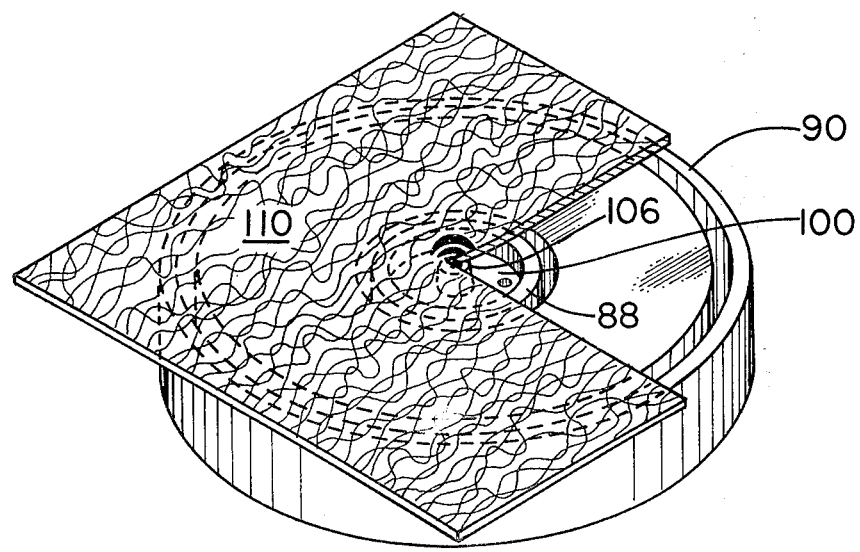

As Table II indicates, the characteristics of the resulting webs can be varied over a wide range. Unless otherwise stated, wicking determinations were made as schematically shown in FIGS. 17 and 18. As illustrated therein, concentric rings 88, 90 of conductive metal such as copper are fixed on support 92 which may, in turn, be supported within pan 94 or other liquid container by means of legs 96 having leveling adjusting bolts 98. Ring 88 may be maintained in position by central disk 100, and ring 90 by stops 102. Conduit 104 provides water from a pump (not shown) to nozzle 106 at the center of disk 100. Overflow is allowed to empty into pan 94 by conduit 108. In use, the web 110 to be tested is placed over both rings. The sample size is not critical so long as both rings are covered. Current is applied to the circuit formed by the rings and water is then pumped to the nozzle 106. The rate of water flow depends to some extent on the absorptive characteristics of the materials; it is important that an excess of water be present at the center and materials be compared at the same flow rates. For these tests a flow rate of 8.0 milliters per minute was used. When the wicking water reaches ring 90, a distance of 1-1/16 inches from ring 88, the circuit is completed and the time required for this travel is noted from the timer. This provides a measure of the web wicking characteristics.

TABLE II

| Run | Bonding | Hand | Average Web Weight | Capillary Absorbency at 5 cm. Water Pressure g.absorbed/g.fiber | 1000G water retention | Average wicking |
|---|---|---|---|---|---|---|
| A | fused | good, soft | 0.0180g/in.$^2$ | 21.91 | 21.98g/g. | 7.20 min. |
| B | contact | very good | 0.0185g/in.$^2$ | 18.25 | 26.24g/g | 7.09 min. |
| C | none | very poor-stiff harsh | 0.0235g/in.$^2$ | 17.87 | 22.35g/g | 30.16 min. |

For the purpose of more closely approximating wicking times for bodily fluids, tests were made as above described using a standard physiological saline solution on webs prepared as in Example 2. As shown in Table III, the wicking times for saline show a dramatic decrease over those for water. This result is very unexpected and highly significant for applications such as diapers, sanitary napkins, tampons, surgical sponges, and the like.

TABLE III

| Run | % Phosphorus | Extrusion Gauge | Average Weight | H$_2$O Wicking @8 ml./min. | Saline Wicking @8 ml./min. |
|---|---|---|---|---|---|
| A | 5.22 | 19 | 0.0339 g/in.$^2$ | 1.73 | 0.31 |
| B | 4.70 | 19 | 0.0322 g/in.$^2$ | 2.14 | 0.32 |
| C | 5.55 | 19 | 0.0262 g/in.$^2$ | 1.87 | 0.25 |
| D | 5.55 | 19 | 0.0320 g/in.$^2$ | 9.54 | 0.36 |

TABLE IV summarizes Examples 1 to 7; under the column "Chemical Modification", "P", "CMC", and "A" refer to phosphorylation, carboxymethylation, and acrylonitrile grafting, respectively. Under the column "Refining", "L" indicates little significant refining, "M" indicates up to about 3 minutes as described in the examples, and "H" indicates greater than about 3 minutes refining time. Under the column "Water Retention" results are reported in grams of water remaining per gram of dry fiber after centrifuging as in U.S. Pat. No. 3,670,069 to Mitchell et al. Under the "Wicking" column, results are reported in terms of time at 8.0 mls per minute flow for webs as described with reference to FIGS. 17 and 18 and in terms of wicking time for a distance of 1-1/16 inches from a static pool for filaments. "Capillary Absorbency" results are reported in terms of grams of water per gram of dry fiber at 5 cm. water pressure using the process described in U.S. Pat. No. 3,658,790 to Bernardin. Under the "Bonding" column, "C" indicates contact bonds, "F" indicates fused bonds, and "N" indicates substantially no bonding. In Example 5 cotton fibers were used while all other examples utilized wood fibers.

TABLE IV

| Example | Chemical Modification | Product | Bonding | Refining | Water Retention | Average Wicking | Capillary Absorbency |
|---|---|---|---|---|---|---|---|
| 1 | P | Filament | — | M | 12.02 g/g | 2.72 Min. | 17.9 g/g |
| 2 | P | Web | C | M | 12.02 g/g | 0.36 Min. | 17.9 g/g |
| 3 | CMC/P | Filament | — | M | 28.64 g/g | 4.88 Min. | 42.2 g/g |
| 4 | CMC/P | Web (0.012 g/in$^2$) | F | M | 28.64 g/g | 1.57 Min. | 42.2 g/g |
| 5 | P | Web | F | H | 6.89 g/g | 7.86 Min. | 10.5 g/g |
| 6 | CMC | Web | F | M | 39.90 g/g | 5.16 Min. | 50.4 g/g |
| 7 | A | Web | C | L | 63.52 g/g | 1.60 Min. | 52.84 g/g |
| 8A | P | Web (0.018 g/in$^2$) | C | M | 26.24 g/g | 7.09 Min. | 18.25 g/g |
| 8B | P | Web (0.017 g/in$^2$) | C | M | 23.21 g/g | 10.20 Min. | 17.95 g/g |
| 8C | P | Web (0.020 g/in$^2$) | N | M | 21.69 g/g | 2.07 Min. | 18.95 g/g |
| 8D | P | Web (0.027 g/in$^2$) | C | M | 22.41 g/g | 10.32 Min. | 19.22 g/g |
| 9A | P | Web (0.018 g/in$^2$) | F | M | 21.98 g/g | 7.20 Min. | 21.91 g/g |
| 9B | P | Web (0.018 g/in$^2$) | C | M | 26.24 g/g | 7.09 Min. | 18.25 g/g |
| 9C | P | Web (0.024 g/in$^2$) | C | M | 22.35 g/g | 30.19 Min. | 17.87 g/g |
| Fluff | — | Batt (0.116 g/in$^2$) | — | — | 0.567 g/g | 0.31 Min. | 6.55 g/g |

EXAMPLE 10

Figure 12:
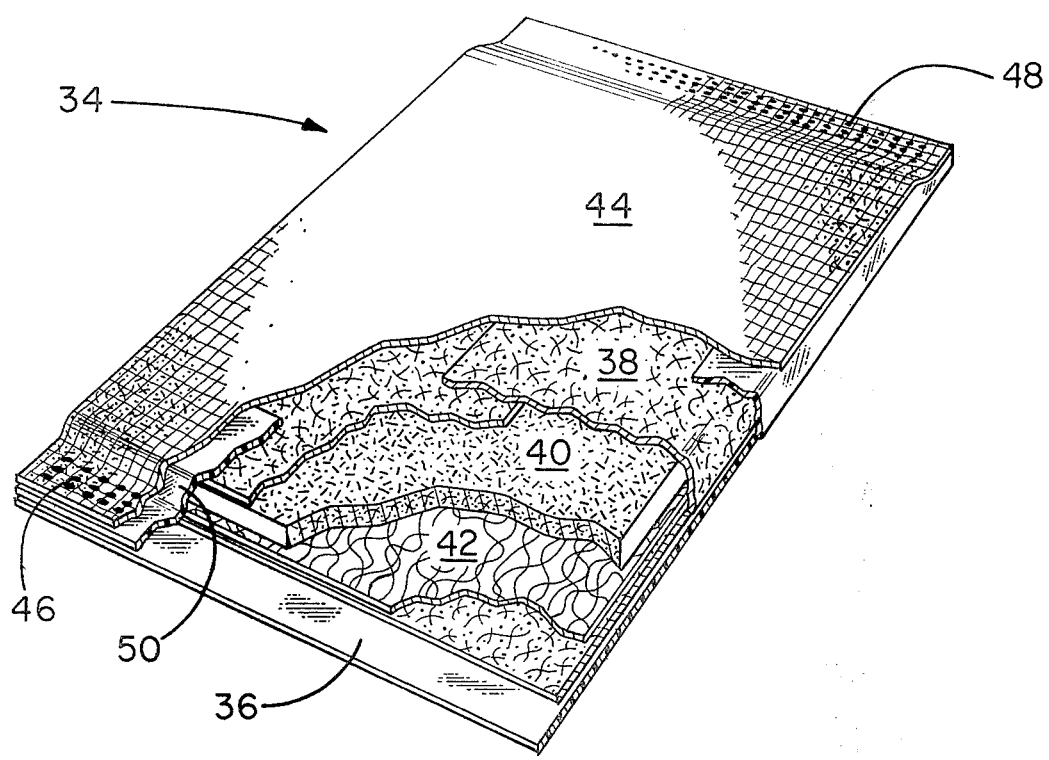
FIG. 12 illustrates in partial section a disposable diaper utilizing the web of FIG. 8.

Disposable diapers are known and may be formed in varying constructions. In general, however, they include an impervious backing, an absorbent layer, and a liner to separate the absorbent material from the skin of the wearer and to help maintain the integrity of the structure. FIG. 12 illustrates an embodiment of such a diaper incorporating the filaments of the present invention. As shown, the diaper 34 includes plastic backing 36, tissue or like layer 38 enclosing absorbent layers 40 which may be fluff and 42 which is a web produced in accordance with the present invention. Liner 44 may be a scrim material having a light cotton applique, for example. The layers may be bonded at ends 46, 48 by heat sealing or adhesives as desired. In a preferred construction plastic covers 50 are provided at both ends to reduce leakage. Reference may be made to Endres U.S. Pat. No. 3,520,303 for further details as to disposable diaper constructions and manufacture.

The web of the present invention provides an easily handleable, non-linting, highly absorbent layer that aids the concentration of liquid excrement away from the surface adjacent the wearer and its wicking characteristics allow significantly improved fluid distribution.

EXAMPLE 11

Figure 13:
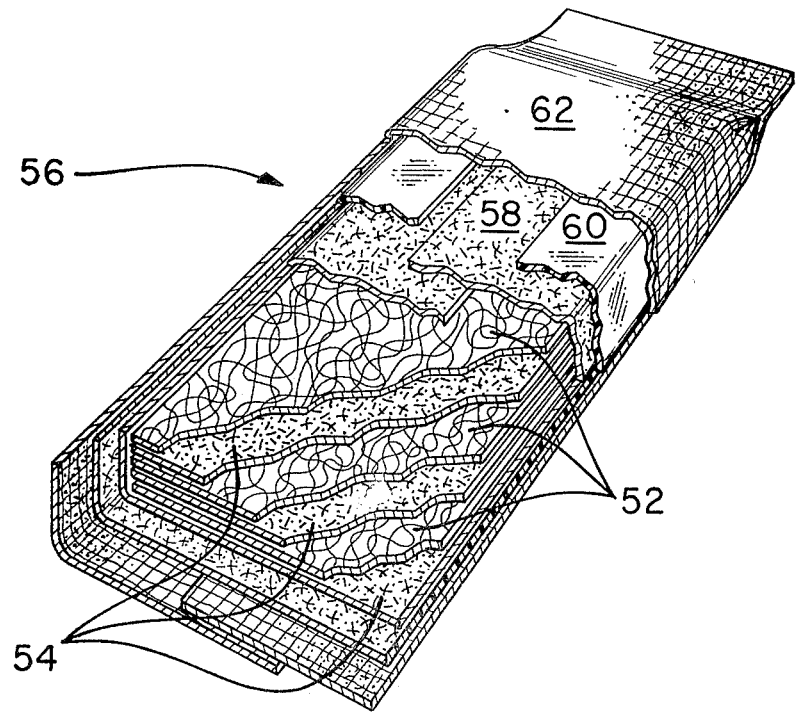
FIG. 13 illustrates also in partial section a sanitary napkin incorporating the web of FIG. 8.

Sanitary napkins are also available in many different forms, most of which can be improved through the incorporation of the webs and filaments of the present invention. For example, FIG. 13 illustrates a sanitary napkin 56 wherein the absorbent core is formed of alternating layers of webs 52 of the present invention and webs or batts 54 of conventional absorbent material such as fluff. The sanitary napkin 56 also includes liner 58 which may be tissue or like material, baffle 60 of a liquid impervious material, and pervious wrapper 62 which may be a scrim material with an applique of fibers. Further description of sanitary napkin configurations may be found by reference to U.S. Pat. No. 3,665,992 to Skora, for example.

Webs of the present invention provide good absorbency with low volumes of material in a particularly convenient form when compared with other available structures.

EXAMPLE 12

There are known many kinds of wiping materials having a variety of uses. For example, U.S. Pat. No. 3,674,617 to Mattes describes a cosmetic wipe and U.S. Pat. No. 3,520,016 to Meitner discloses a different absorbent wiper. The filaments and webs of the present invention are particularly useful in producing highly absorbent wipes due to their ease of handling and less linting characteristics. Also, the resulting products exhibit the ability to reabsorb substantial liquid quantities after only moderate wringing out.

Figure 14:
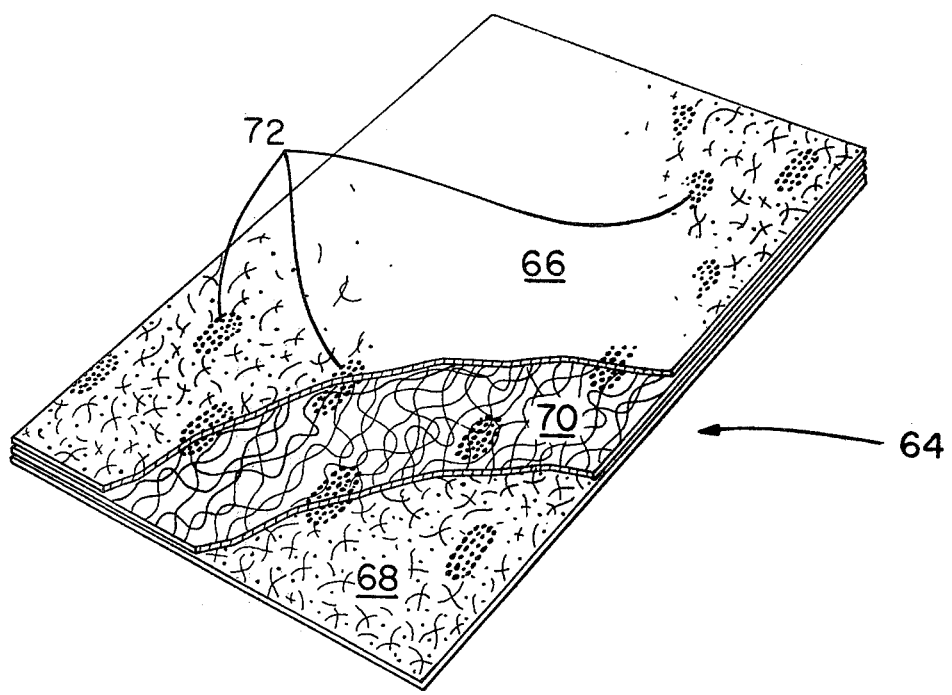
FIG. 14 similarly illustrates a wipe incorporating the web of FIG. 8.

An example of such a wipe is shown in FIG. 14 which illustrates wipe 64 including surface layers 66, 68 of a tissue or like material and a central layer 70 of a web of the present invention. Embossments 72 provide for interlayer bonding and can provide a fabric-like feel and limpness. It will be recognized that for a more durable structure a woven material may be used for the surface layers as described in the above-mentioned Meitner patent, for example.

EXAMPLE 13

Surgical sponges are conventionally used during operations for absorbing bodily fluids and generally include an absorbent layer surrounded by a liquid pervious woven material such as gauze. Because of the danger inherent in allowing foreign material into the surgical incision, it is important that surgical sponges be non-limiting.

Figure 15:
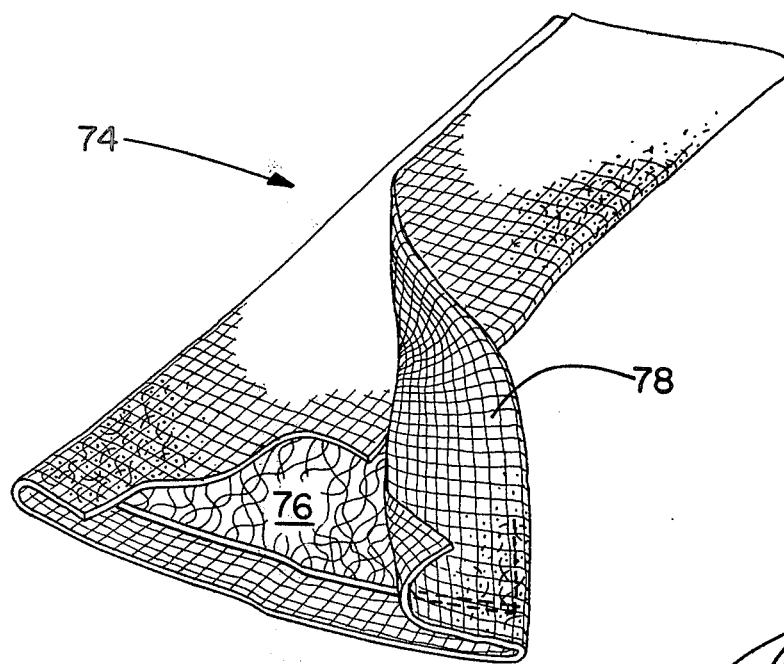
FIG. 15 illustrates a surgical sponge incorporating the web of FIG. 8 folded away for clarity.

FIG. 15 illustrates an embodiment of a surgical sponge 74 including a web 76 of the filaments of the present invention and woven wrapper 78. The combination presents a highly absorbent sponge with fast wicking rates and low linting characteristics.

EXAMPLE 14

Figure 16:
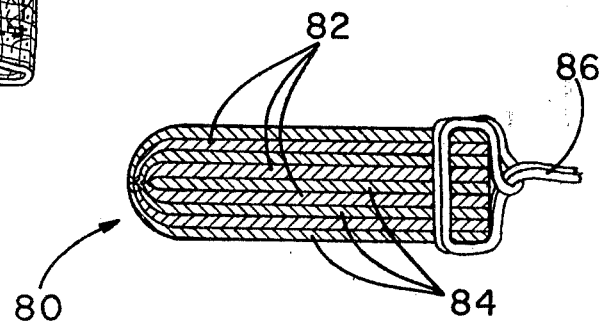
FIG. 16 illustrates in partial section a tampon incorporating the web of FIG. 8.

FIG. 16 illustrates in cross-section an improved tampon 80 incorporating the filaments of the present invention. While other tampon constructions will benefit from the use of the filaments of the present invention, the illustrated one includes alternate layers of the web of the present invention 82 and other absorbent material 84 such as fluff, for example. String 86 is provided for ease of removal. The filaments of the present invention provide high absorbency and fuller utilization of the conventional absorbent material.

For additional details of tampon structures and their manufacture, reference may be made to U.S. Pat. Nos. 3,643,661 to Crockford; 3,683,912 to Olson et al; and 3,683,915 to Voss; for example.

While absorbent batts of chemically modified fibers have been formed, such batts have had very small pores that inhibit fluid transfer. In contrast, batts formed from continuous or chopped filaments of the present invention maintain relatively open pores even after being wet and redried so that liquid transfer is greatly increased. Furthermore, batts of filaments formed in accordance with the present invention are less linting than batts of conventional materials.

Thus it is apparent that there has been provided, in accordance with the invention, chemically modified filaments, webs, and structures embodying such filaments and webs that fully satisfy the objects, aims, and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications, and variations as fall within the spirit and broad scope of the appended claims.

I claim:

1. A highly absorbent, fast wicking filament comprising fibers of a chemically modified cellulose, which has been transformed by derivatization to increase its hydrophilic character, said fibers being selected from the group consisting of,
    (a) cellulose that has been chemically substituted by etherization or esterification,
    (b) cellulose that has been chemically substituted by etherization or esterification and cross-linked, and
    (c) cellulose that has been polymeric grafted, said fibers being generally of papermaking size and having been extruded through an orifice having a diameter of about 0.005 to about 0.060 inch and interbonded so as to be generally aligned and form channels within said filament for transporting liquid.

2. The filament of claim 1 wherein said chemically modified cellulose fibers comprise phosphorylated wood pulp.

3. The filament of claim 1 wherein said chemically modified cellulose fibers comprise phosphorylated cotton linters.

4. The filament of claim 1 wherein said chemically modified cellulose fibers have been produced by chemical substitution and crosslinking.

5. The filament of claim 4 wherein said chemically modified fibers comprise cross-linked carboxymethyl cellulose.

6. The filament of claim 1 wherein said chemically modified cellulose fibers have been produced by polymer grafting.

7. The filament of claim 6 wherein said chemically modified cellulose fibers comprise hydrolyzed acrylonitrile grafted cellulose.

8. The filament of claim 1 wherein said chemically modified cellulose fibers comprise a blend of fibers selected from the group consisting of chemically substituted cellulose fibers, crosslinked chemically substituted cellulose fibers, and polymer grafted cellulose fibers.

9. A web comprising interbonded filaments of claim 1.

10. A disposable diaper including a backing, absorbent material, and liner wherein the absorbent material includes the filaments of claim 1.

11. A sanitary napkin comprising a liner and an absorbent material wherein the absorbent material includes the filaments of claim 1.

12. A wipe comprising an absorbent layer including the filaments of claim 1.

13. A tampon comprising an absorbent material including the filaments of claim 1.

14. A surgical sponge comprising an absorbent material including the filaments of claim 1.

15. An absorbent dressing useful as a sanitary protection device including as an essential ingredient a layer comprising the filaments of claim 1.

* * * * *